(12) United States Patent
Spencer et al.

(10) Patent No.: US 10,267,720 B2
(45) Date of Patent: Apr. 23, 2019

(54) APPARATUS FOR ELECTRICALLY MEASURING INDIVIDUAL PARTICLES FLOWING IN A LIQUID

(71) Applicant: University of Southampton, Southampton (GB)

(72) Inventors: Daniel Christopher Spencer, Southampton (GB); Hywel Morgan, Southampton (GB)

(73) Assignee: University of Southampton, Southampton (GB)

(*) Notice: Subject to any disclaimer, the term of this patent is extended or adjusted under 35 U.S.C. 154(b) by 138 days.

(21) Appl. No.: 14/392,104

(22) PCT Filed: Apr. 15, 2014

(86) PCT No.: PCT/GB2014/000146
§ 371 (c)(1),
(2) Date: Oct. 14, 2015

(87) PCT Pub. No.: WO2014/170625
PCT Pub. Date: Oct. 23, 2014

(65) Prior Publication Data
US 2016/0041081 A1 Feb. 11, 2016

(30) Foreign Application Priority Data
Apr. 16, 2013 (GB) .................................. 1306914.1

(51) Int. Cl.
*G01N 15/10* (2006.01)
*G01N 15/12* (2006.01)

(52) U.S. Cl.
CPC ..... *G01N 15/1031* (2013.01); *G01N 15/1056* (2013.01); *G01N 2015/1254* (2013.01)

(58) Field of Classification Search
USPC ................................ 324/649, 71.1, 452, 453
See application file for complete search history.

(56) References Cited

U.S. PATENT DOCUMENTS 3,530,713 A * 9/1970 Nazareth, Jr. ............. G01F 1/58
73/861.12
3,944,917 A * 3/1976 Hogg .................. G01N 15/1227
324/442
(Continued)

FOREIGN PATENT DOCUMENTS

EP 1335198 A1 8/2003
EP 2211164 A1 7/2010
(Continued)

OTHER PUBLICATIONS

Barat et al., "Simultaneous High Speed Optical and Impedance Analysis of Single Particles With a Microfluidic Cytometer", Lab on a Chip, The Royal Society of Chemistry, 2012, 12, 118, pp. 118-126.
(Continued)

*Primary Examiner* — Vincent Q Nguyen
(74) *Attorney, Agent, or Firm* — Iandiorio Teska & Coleman, LLP

(57) ABSTRACT

Apparatus (3) for electrically measuring individual particles (4) flowing in a liquid (6), which apparatus (3) comprises: (i) a fluidic channel (5) for receiving a liquid (6) having the individual particles (4) in suspension in the liquid (6); (ii) a first electrode arrangement (8) having at least one measurement electrode (16) and at least one signal electrode (11); (iii) at least one other electrode arrangement (9) having at least one measurement electrode and at least one signal electrode (13); (iv) at least one signal conditioning electrode (10, 12, 14, 15, 17, 19) positioned adjacent to at least one of the measurement electrodes (16, 18) or at least one of the signal electrode (9); and (v) measuring means (20, 21) for measuring electrical signal changes; and the apparatus (3) being such that: (vi) the first and the other electrode arrangements (8, 9) are connected to the measuring means (20, 21) whereby individual particles passing between the first and other electrode arrangements (8, 9) cause a change in
(Continued)

Block diagram to perform measurement for standard 4 electrode design.

electrical signal which is measured; and (vii) the electrical potential of the signal conditioning electrode (10, 12, 14, 15, 17, 19) is controlled to substantially prevent current flow between the first electrode arrangement (8) and the other electrode arrangement (9).

19 Claims, 23 Drawing Sheets

(56) References Cited

U.S. PATENT DOCUMENTS

| | | | |
|---|---|---|---|
| 4,751,842 A | 6/1988 | Ekrann et al. | |
| 5,436,565 A | 7/1995 | Gammell | |
| 6,426,615 B1 | 7/2002 | Mehta | |
| 2003/0102854 A1 | 6/2003 | Gascoyne et al. | |
| 2008/0111563 A1 | 5/2008 | Ott et al. | |
| 2010/0006441 A1* | 1/2010 | Renaud | B01L 3/502746 |
| | | | 204/643 |
| 2011/0031389 A1* | 2/2011 | Reed | G01N 33/48721 |
| | | | 250/282 |
| 2012/0084022 A1* | 4/2012 | Giovangrandi | G01F 1/58 |
| | | | 702/45 |
| 2013/0175171 A1* | 7/2013 | Aizel | B01L 3/502753 |
| | | | 204/453 |
| 2013/0261021 A1* | 10/2013 | Bocchi | B01L 3/5088 |
| | | | 506/9 |
| 2014/0295284 A1* | 10/2014 | Ijiri | H01M 4/587 |
| | | | 429/231.8 |
| 2015/0102822 A1* | 4/2015 | Okuda | G01N 27/62 |
| | | | 324/464 |
| 2016/0041080 A1 | 2/2016 | Spencer et al. | |
| 2016/0059206 A1* | 3/2016 | Chen | G10K 15/00 |
| | | | 210/748.05 |

FOREIGN PATENT DOCUMENTS

| | | |
|---|---|---|
| EP | 2259044 A1 | 12/2010 |
| WO | WO97/15825 | 5/1997 |
| WO | WO03/048728 A2 | 6/2003 |
| WO | WO2007/088517 A2 | 8/2007 |

OTHER PUBLICATIONS

Spencer et al., "Positioning Dependence of Particles in Microfluidic Impedance Cytometry", Lab on a Chip, The Royal Society of Chemistry, 2011, 11, pp. 1234-1239.

Lanz et al., "Differential Impedance Spectrometer and Vision System for Analysis of Single Cells", IEEE, Transducers 2009, Denver, CO, USA, Jun. 21-25, 2009, pp. 1297-1300.

T. Sun et al. High Speed Multi-Frequency Impedance Analysis of Single Particles in a Microfluidic Cytometer Using Maximum Length Sequences, Lab on a Chip, vol. 7, pp. 1030-1040 (published Jun. 8, 2007).

* cited by examiner

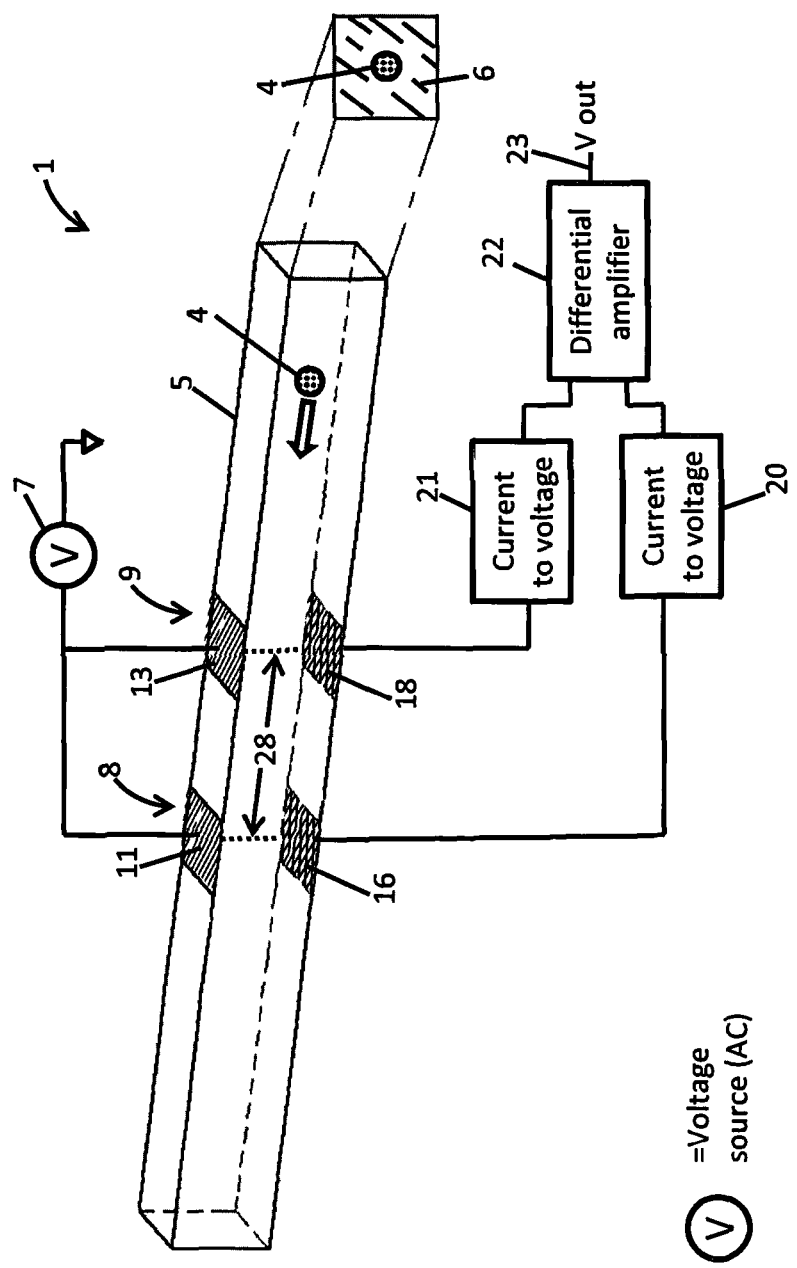
Figure 1. Block diagram to perform measurement for standard 4 electrode design.

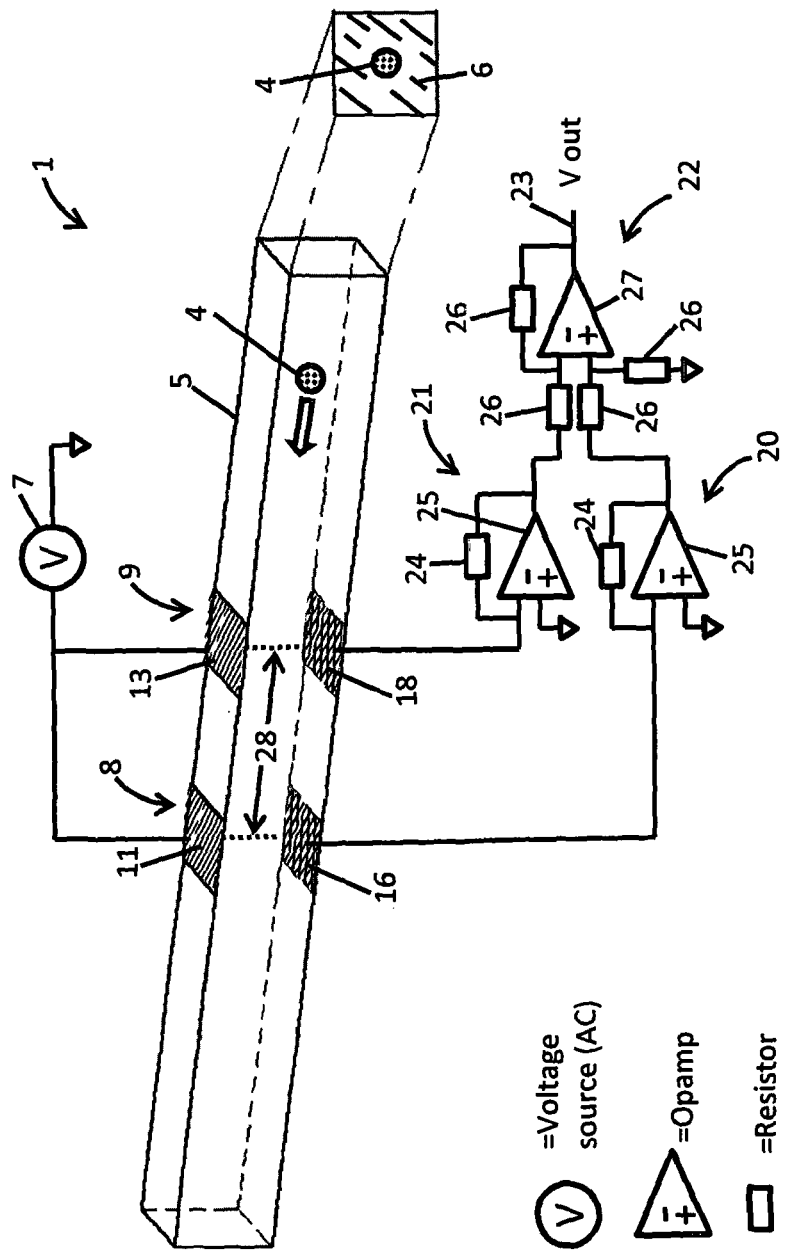
Figure 2. Circuit diagram to perform measurement for standard 4 electrode design.

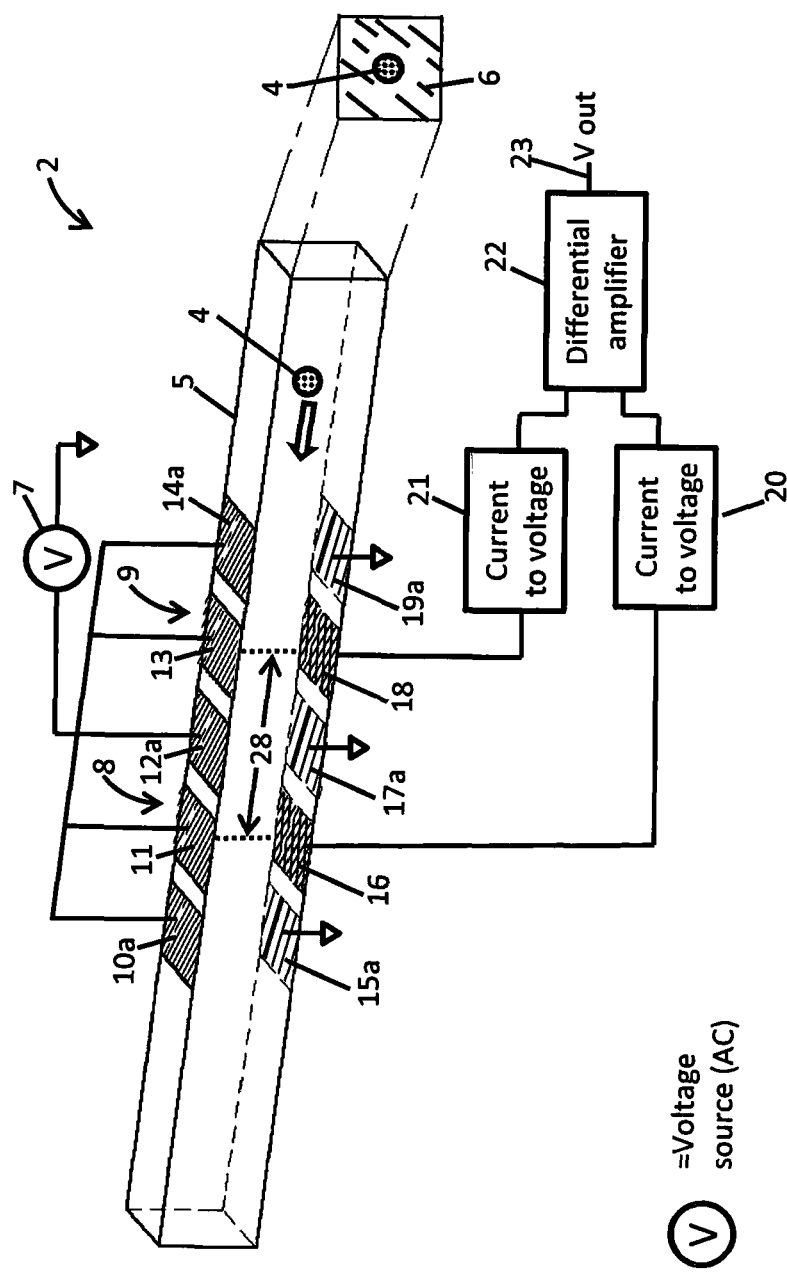
Figure 3. Block diagram to perform measurement for standard guard electrode design.

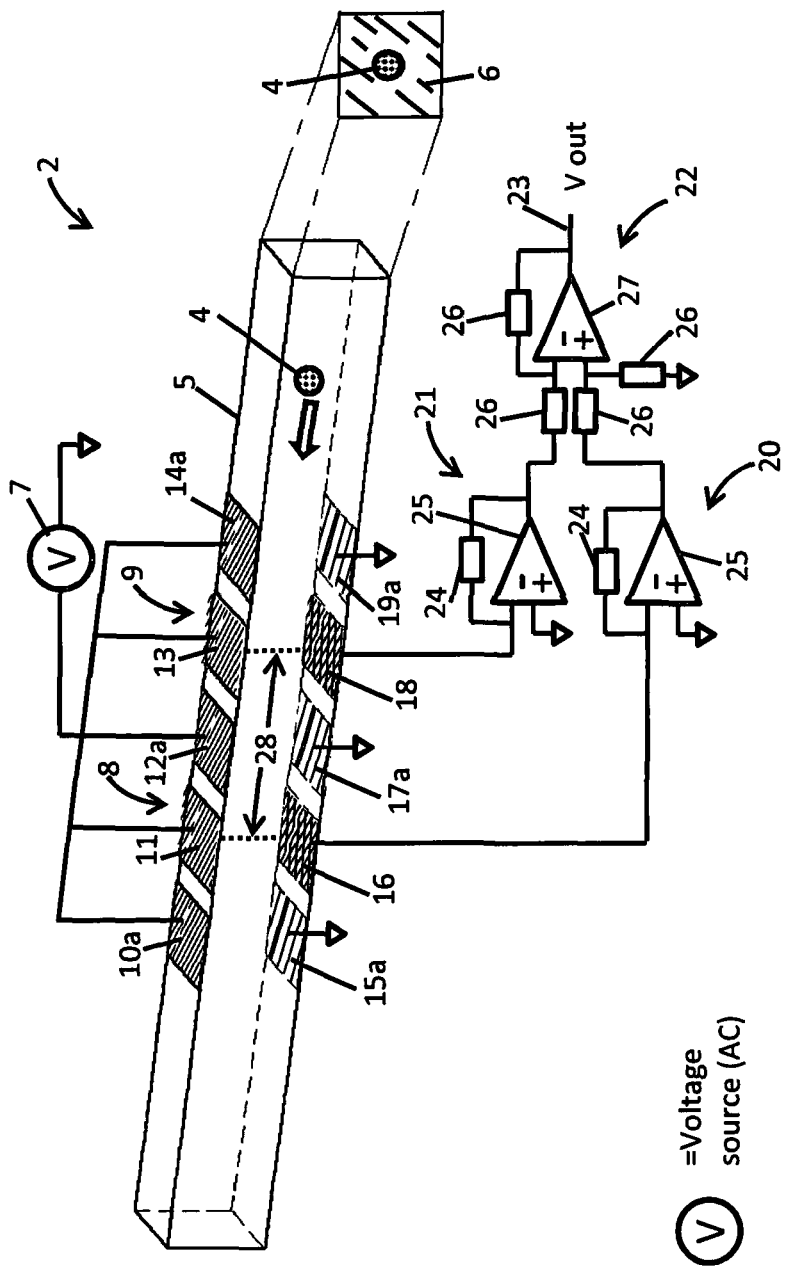
Figure 4. Circuit diagram to perform measurement for standard guard electrode design.

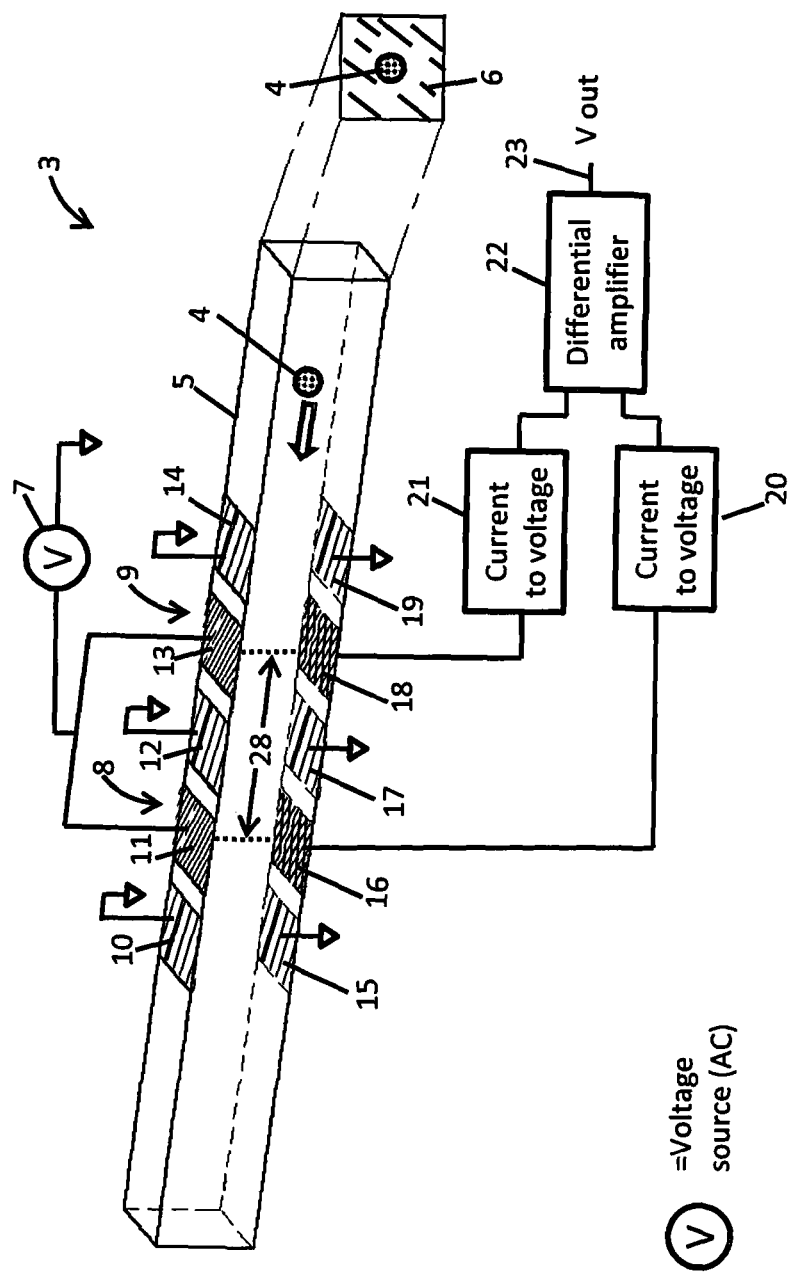
Figure 5. Block diagram to perform measurement for new electrode design.

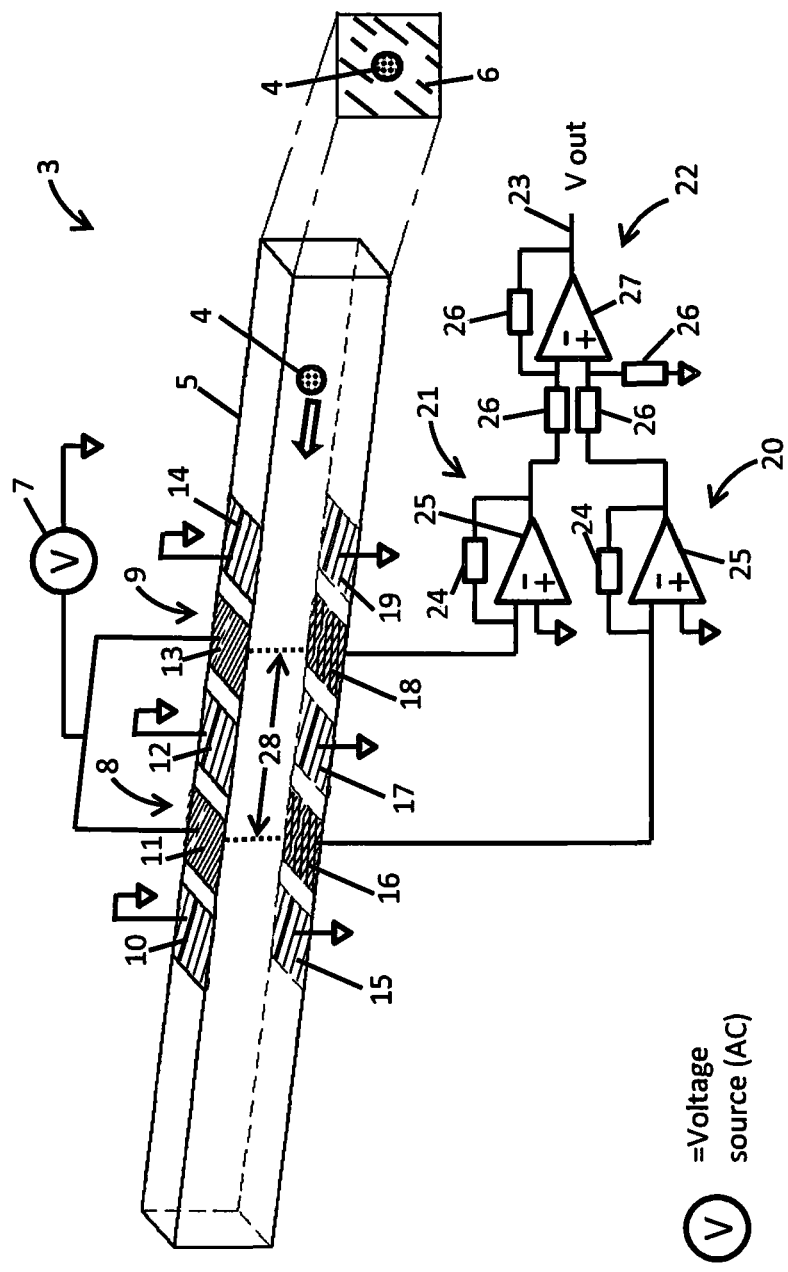
Figure 6. Circuit diagram to perform measurement for new electrode design.

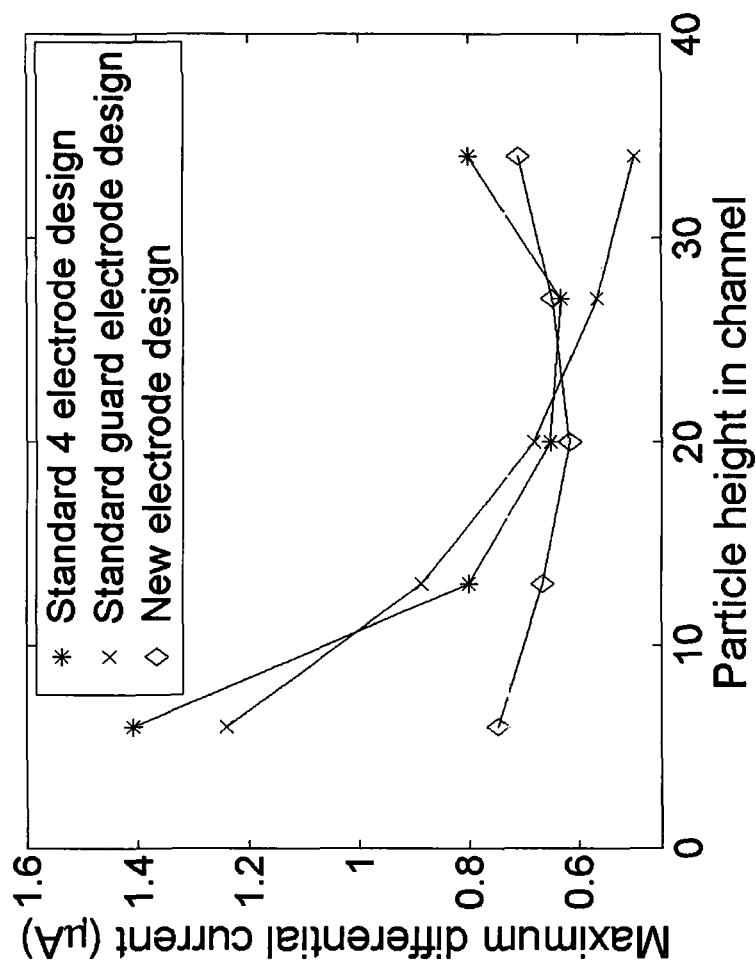
Figure 7. Simulated variation in differential current (impedance signal) with particle height for the 3 electrode designs shown in Figures 1-6.

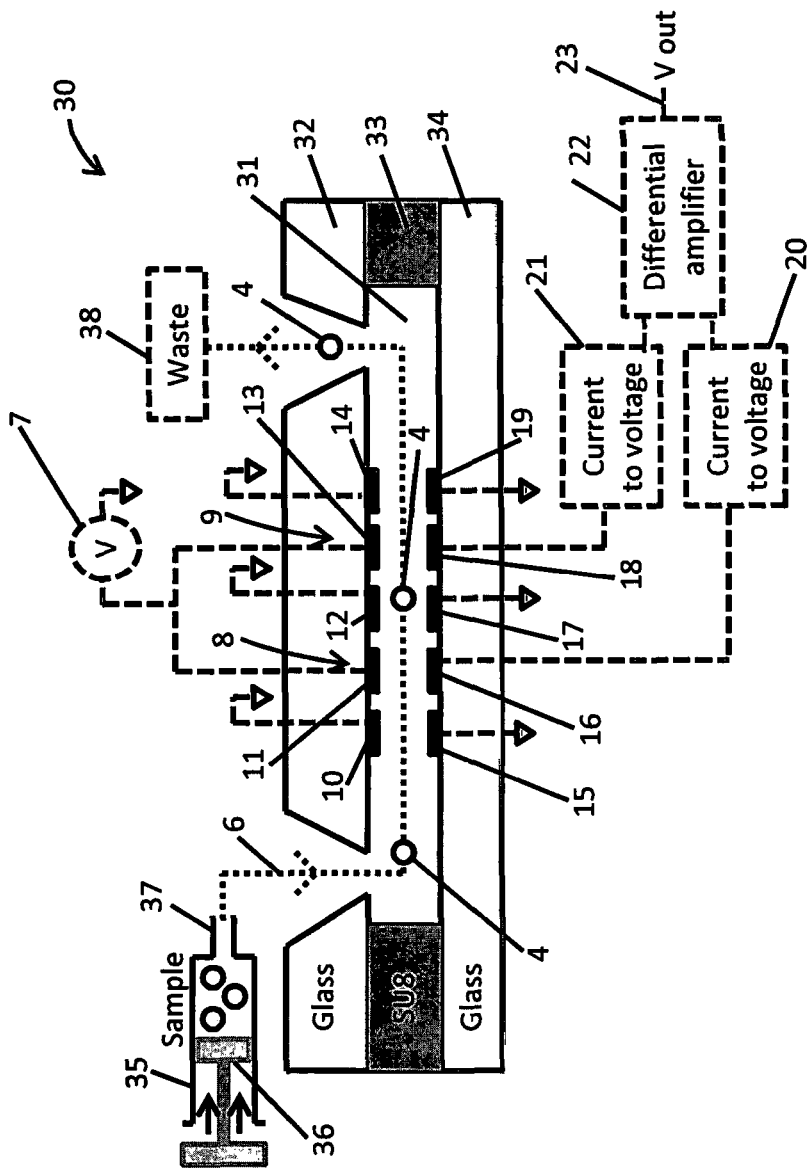
Figure 8. Overview of operation of the new electrode design.

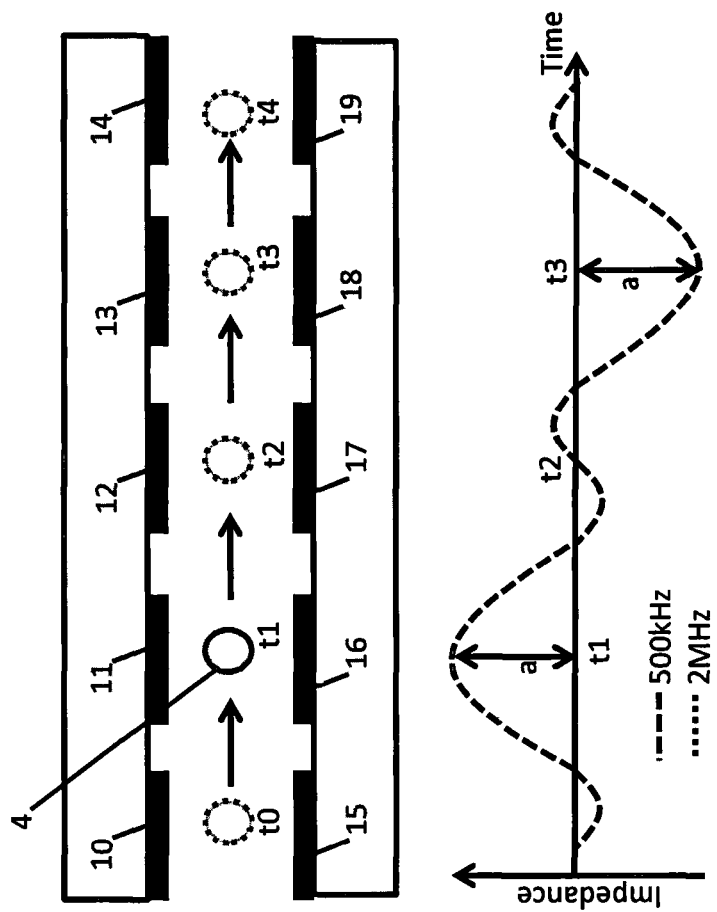
Figure 9. Overview of operation of the new electrode design.

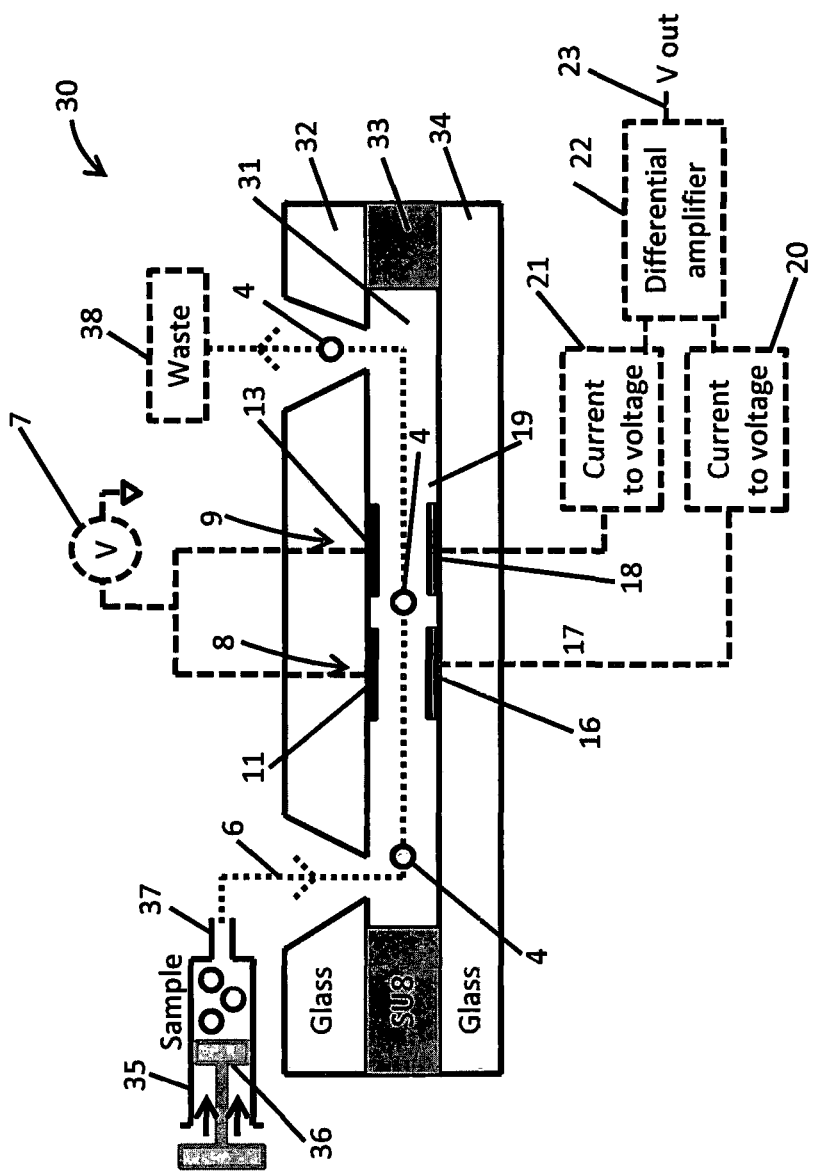
Figure 10. Overview of operation of the standard electrode design.

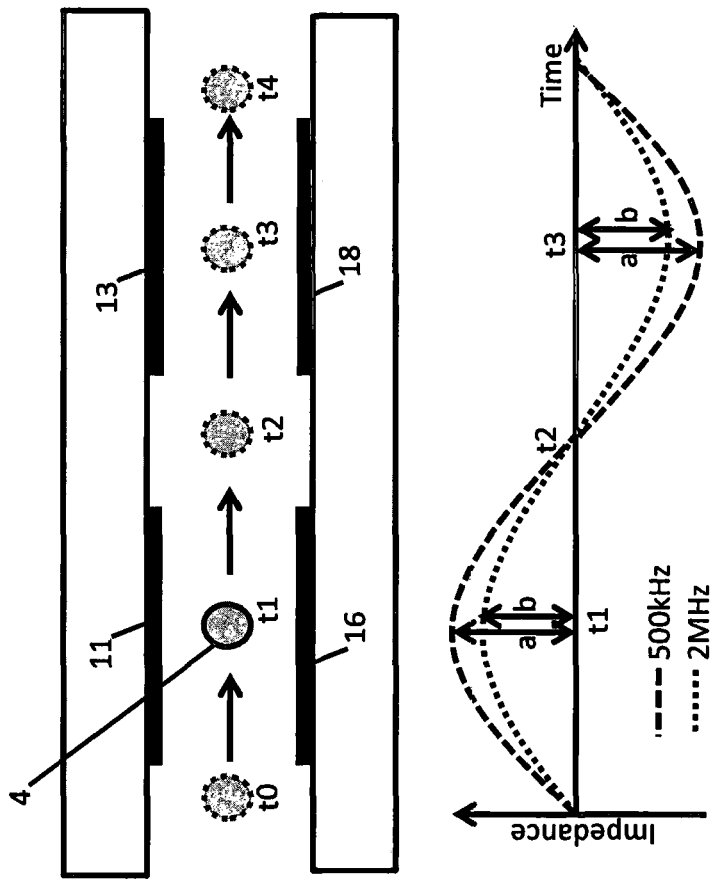
Figure 11. Overview of operation of the standard electrode design.

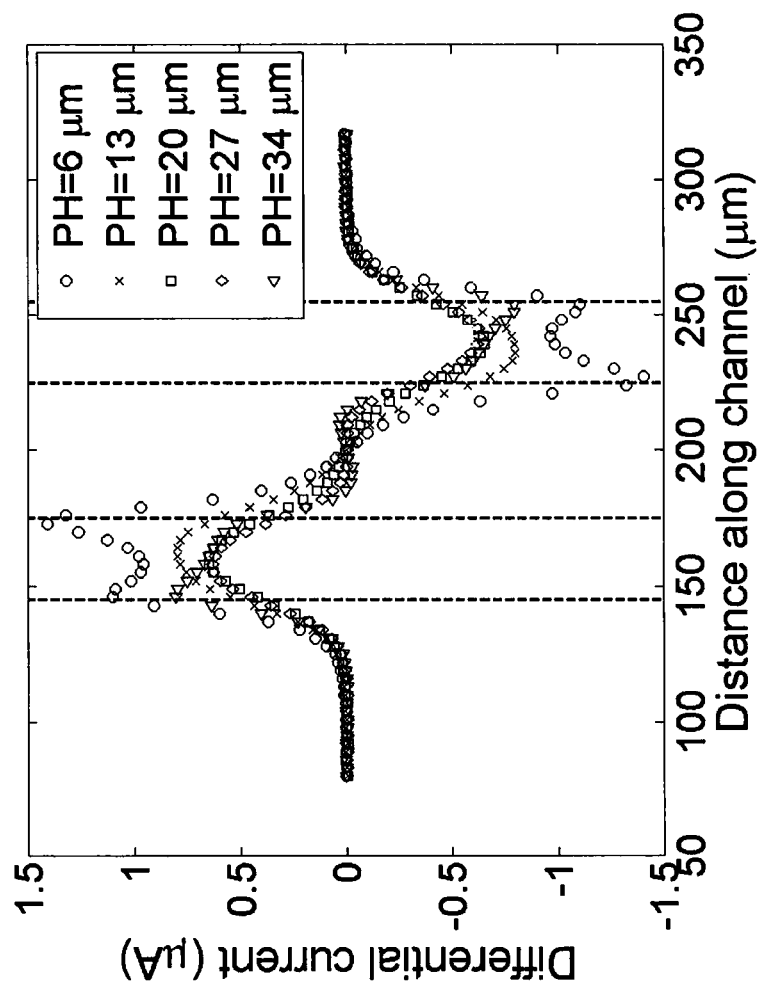
Figure 12. Simulated differential current (impedance spectra) for a 10 μm particle passing at different heights (PH) through the electrodes shown in Figures 1-2.

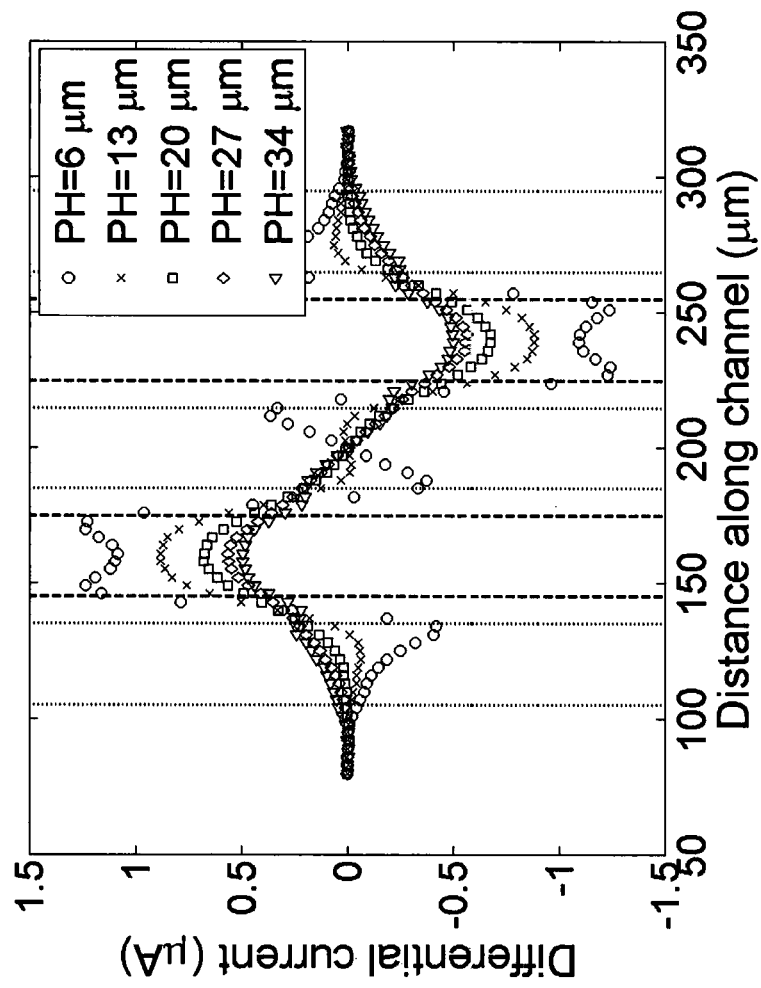
Figure 13. Simulated differential current (impedance spectra) for a 10 μm particle passing at different heights (PH) through the electrodes shown in Figures 3-4.

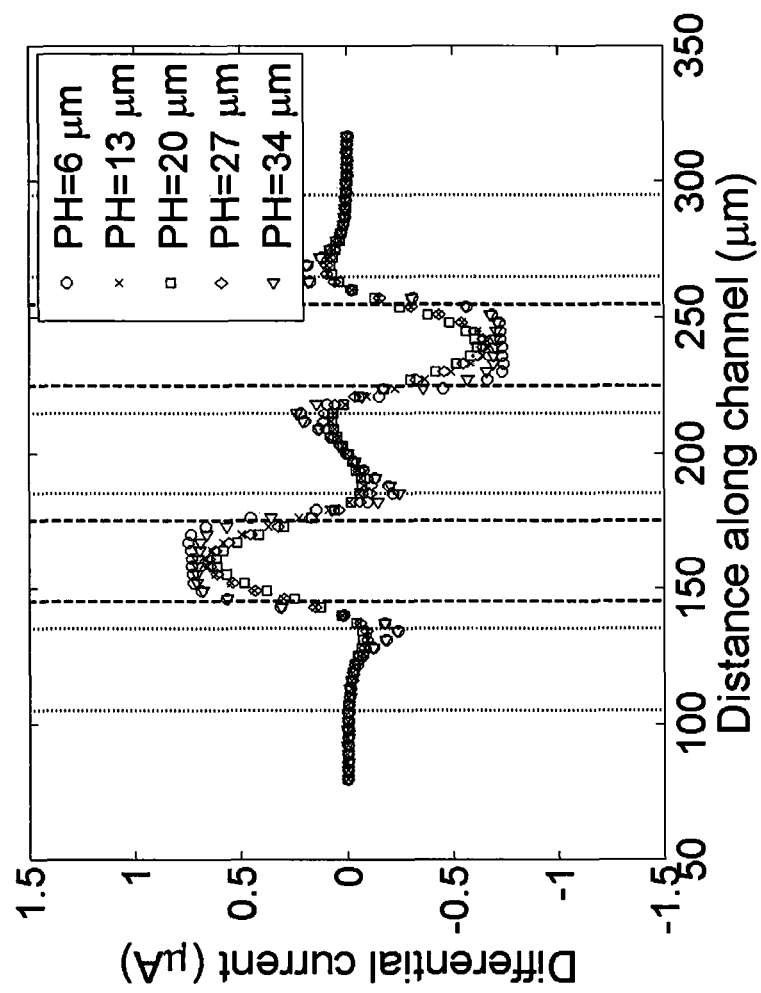
Figure 14. Simulated differential current (impedance spectra) for a 10 μm particle passing at different heights (PH) through the electrodes shown in Figures 5-6.

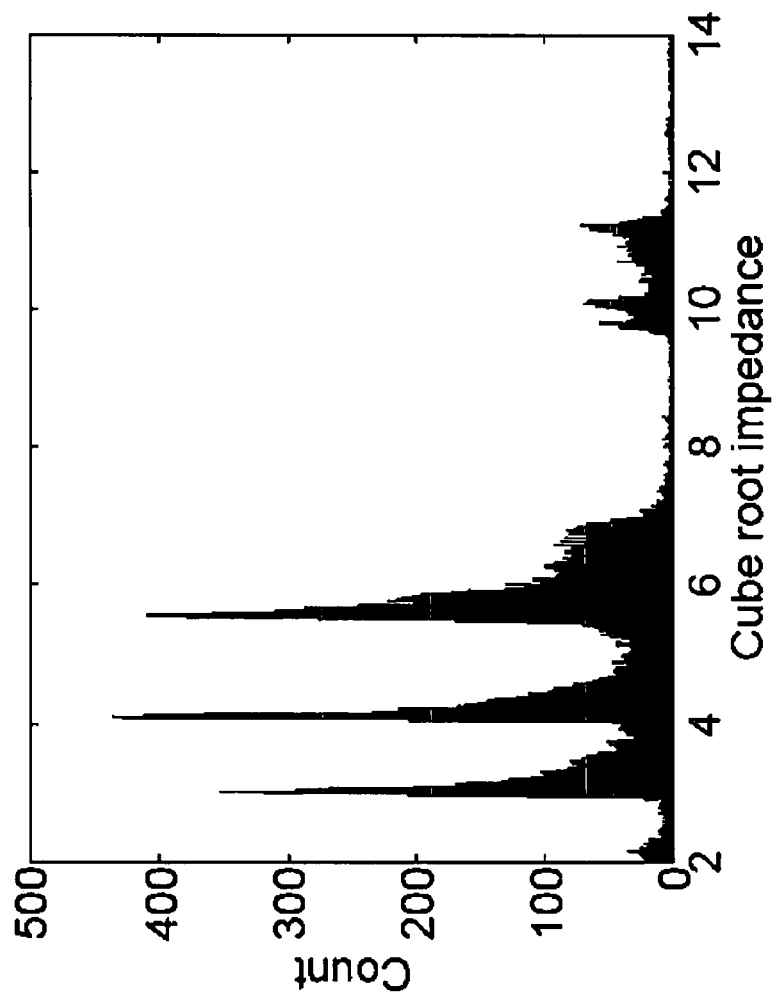
Figure 15. Histogram of a mixture of 3, 4.5, 6 and 10 μm diameter polystyrene beads experimentally measured using the electrode configuration shown in Figures 1-2.

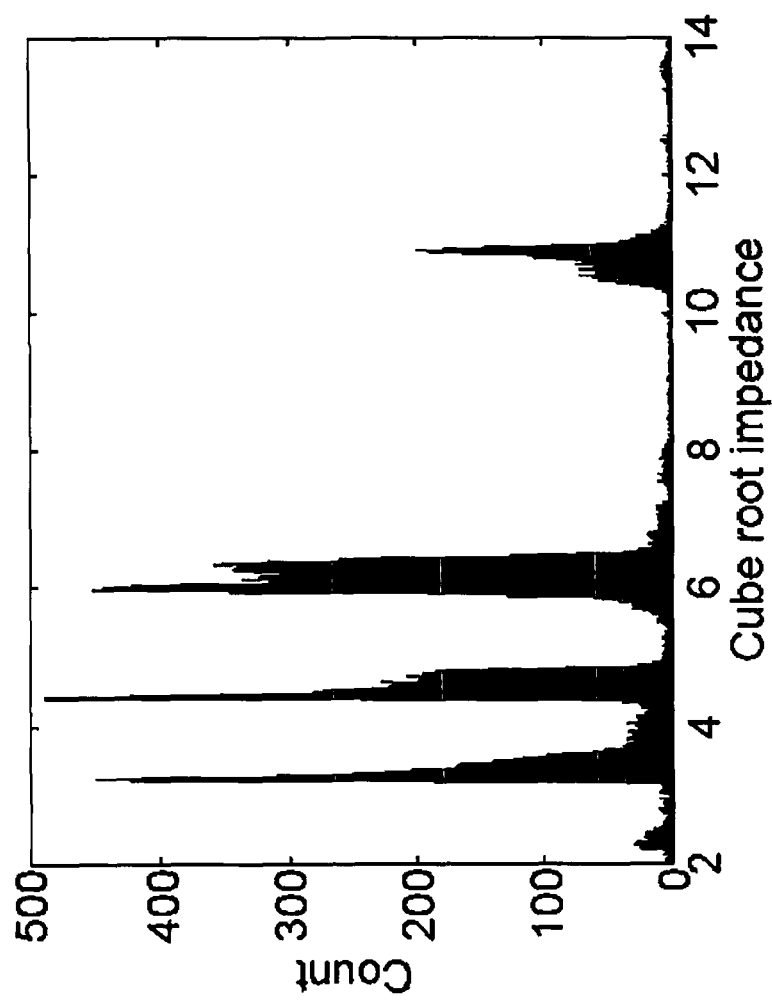
Figure 16. Histogram of a mixture of 3, 4.5, 6 and 10 μm diameter polystyrene beads experimentally measured using the electrode configuration shown in Figures 5-6.

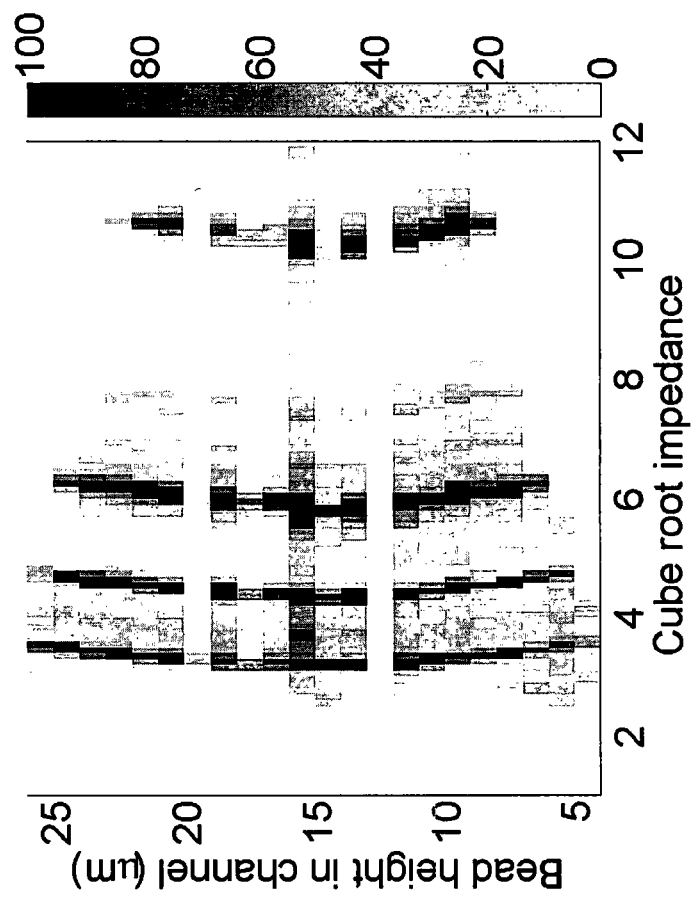
Figure 17. Density plot of a mixture of 3, 4.5, 6 and 10 μm diameter polystyrene beads experimentally measured using the electrode configuration shown in Figures 5-6. The bead height in the channel was estimated by comparing each experimental impedance signal with simulated signal and finding the best match.

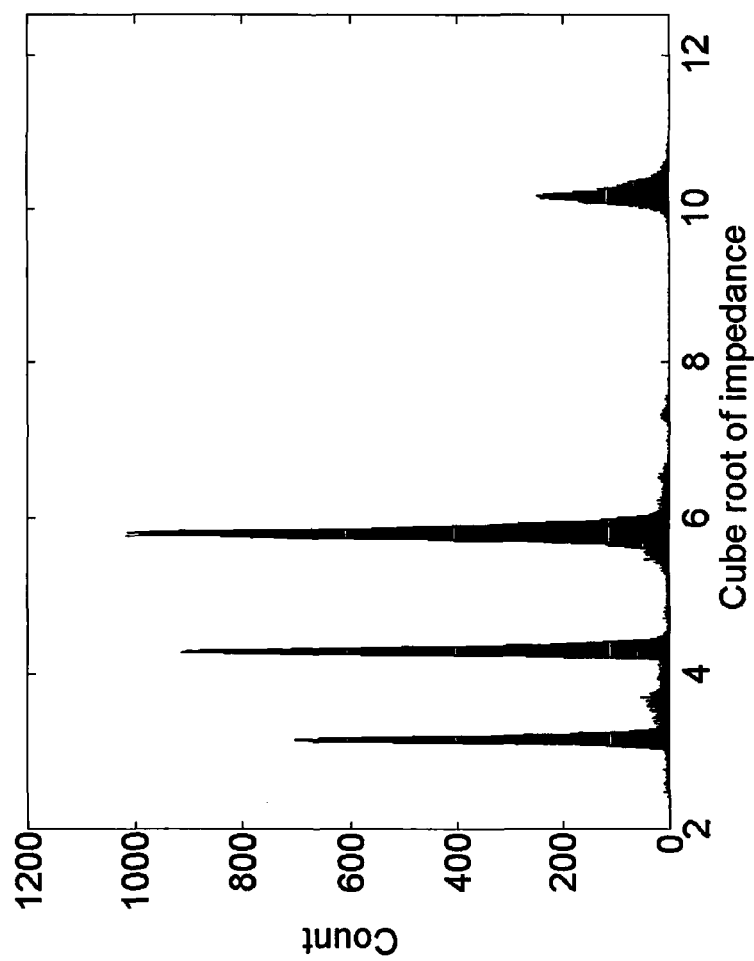
Figure 18. Histogram of the data shown in Figure 16 after correction for particle position.

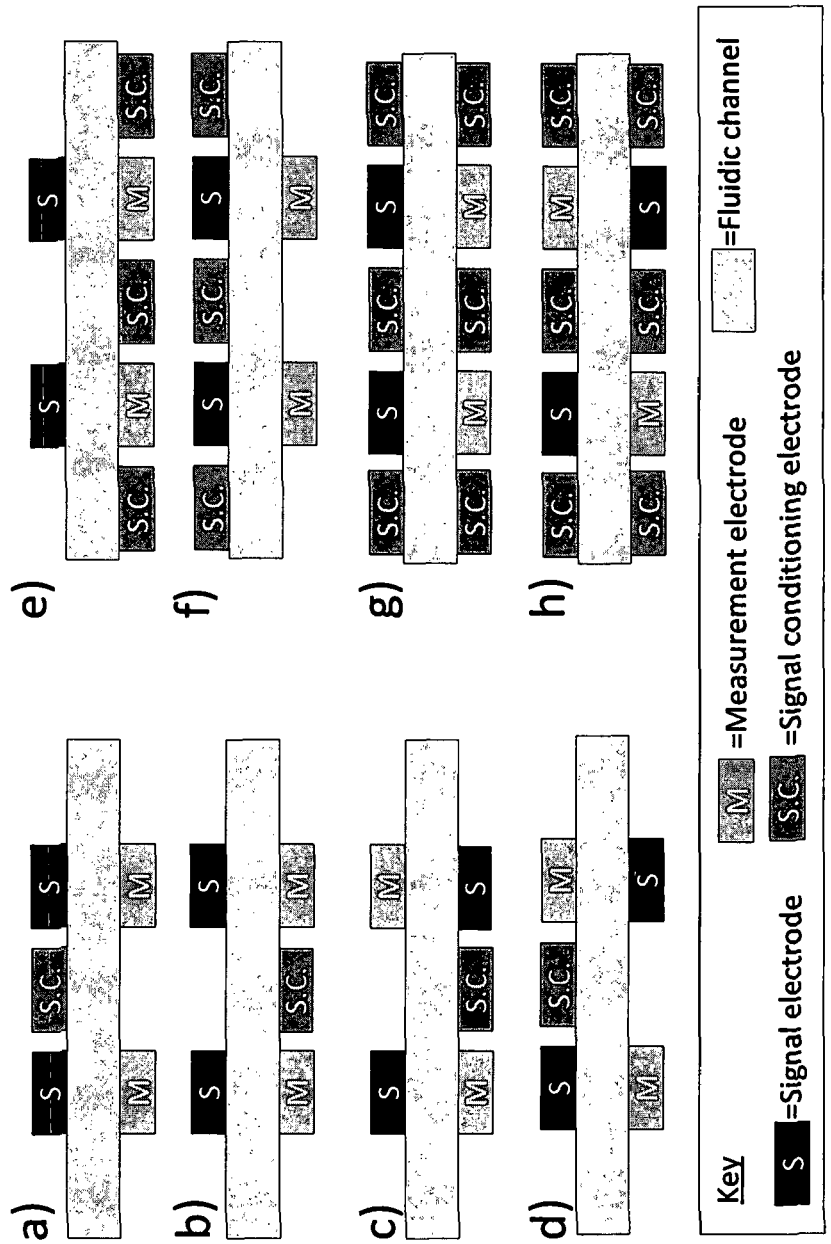
Figure 19a. Different relative positions for signal electrodes, measurement electrodes and signal conditioning electrodes.

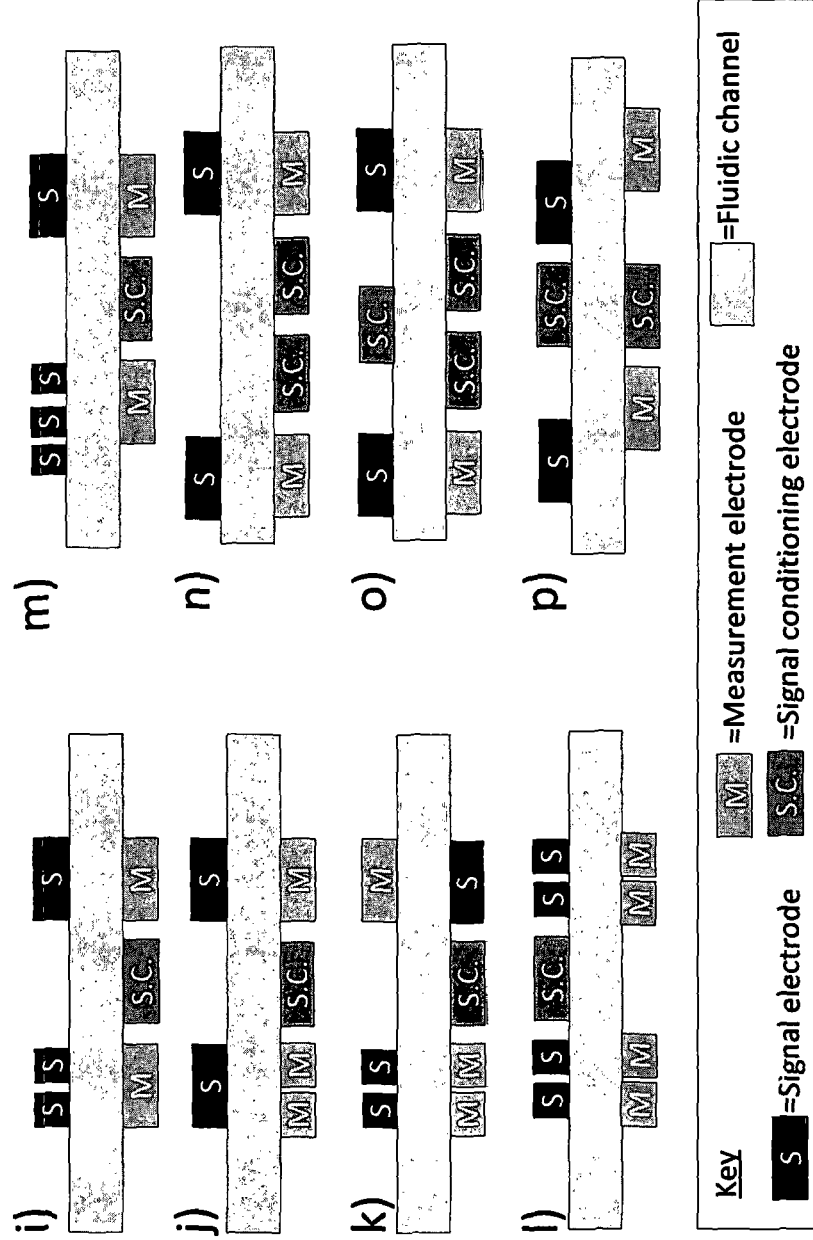
Figure 19b. Different relative positions for signal electrodes, measurement electrodes and signal conditioning electrodes.

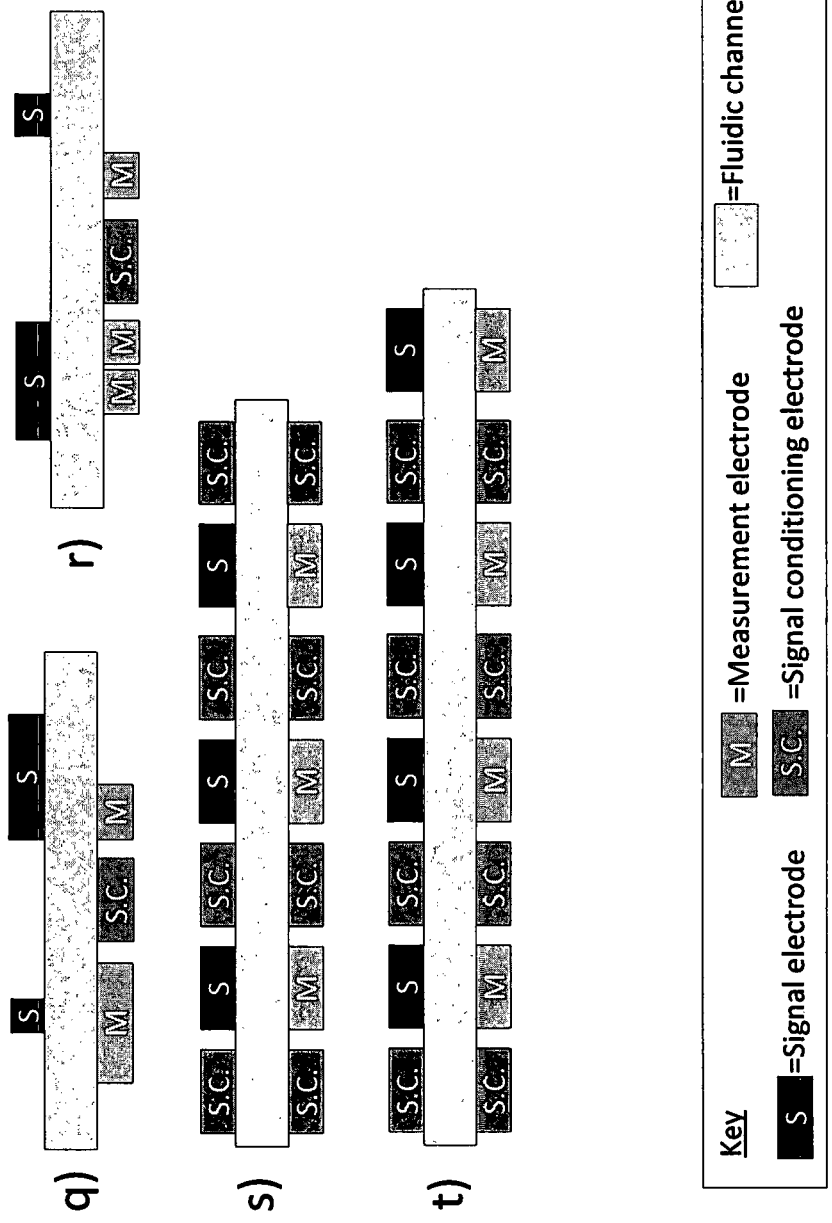
Figure 19c. Different relative positions for signal electrodes, measurement electrodes and signal conditioning electrodes.

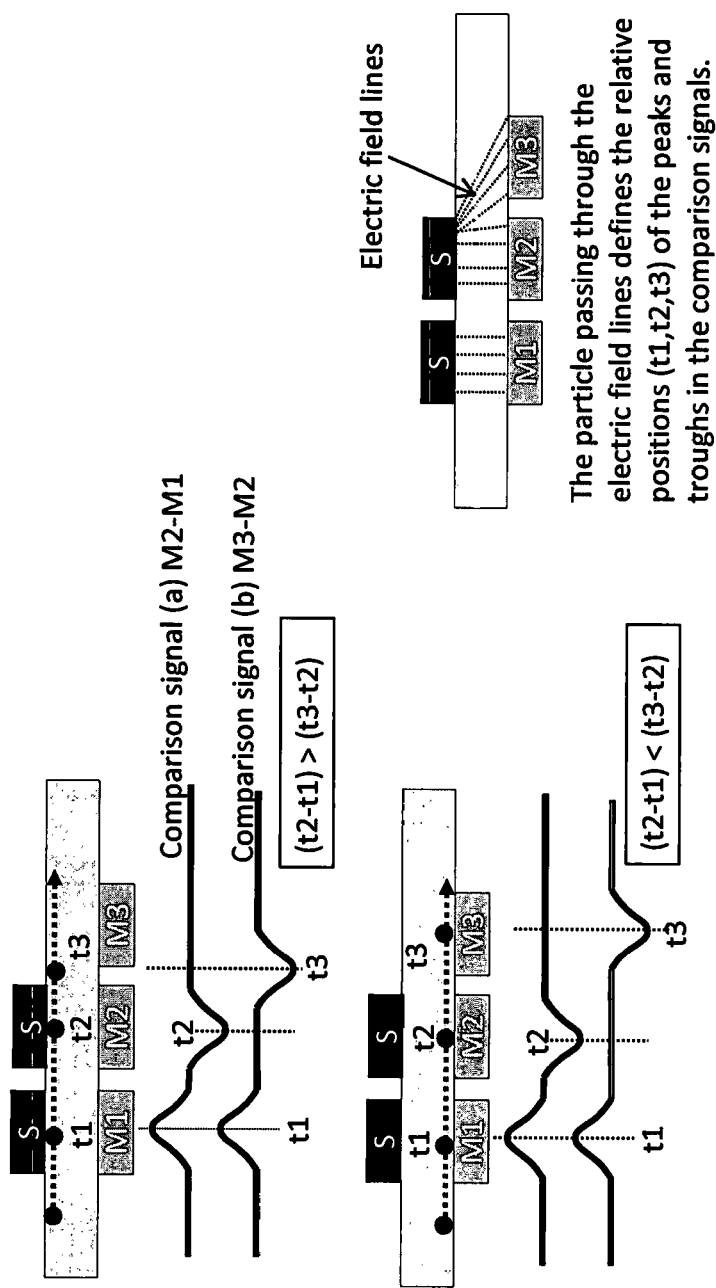
Figure 20. Different steps for measuring electrical signals and generating a comparison signal.

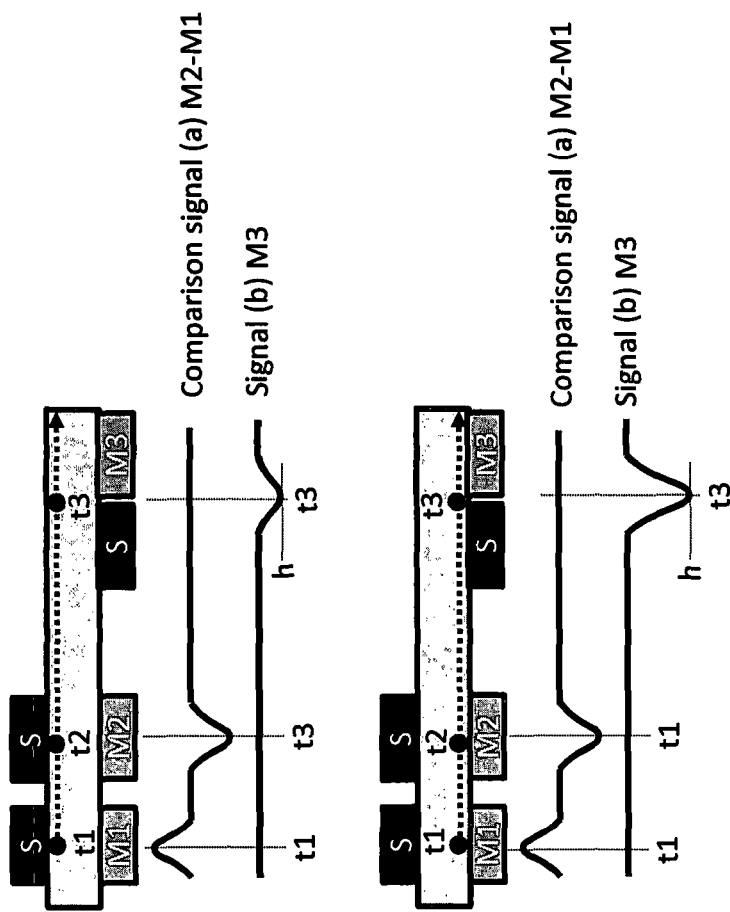
Figure 21. Different steps for measuring electrical signals and generating a comparison signal.

APPARATUS FOR ELECTRICALLY MEASURING INDIVIDUAL PARTICLES FLOWING IN A LIQUID

This invention relates to apparatus for electrically measuring individual particles flowing in a liquid.

The electrical measurement of individual particles flowing in a liquid is known as microfluidic impedance cytometry. Known apparatus for electrically measuring individual particles flowing in a liquid comprises of a fluidic channel for receiving a liquid having the individual particles in suspension in the liquid, a first electrode arrangement having a measurement electrode and a signal electrode, and a second electrode arrangement having a measurement electrode and a signal electrode. The fluidic channel is often known as a microfluidic channel. The first electrode arrangement and the second electrode arrangement are usually miniature measurement electrodes, and they may be fabricated on the top and bottom of the fluidic channel.

In the known apparatus, the individual particles pass in the gap between the first and second electrode arrangements. The individual particles cause a change in electrical current and this change in electrical current is measured and recorded as an impedance signal. A problem exists in that, in the known apparatus, an individual particle travelling close to the electrodes has a higher measured impedance compared to the same sized particle travelling through the centre of the channel. This higher measured impedance is due to the fact that the particle distorts the electric field between the measurement electrodes, and this causes a difference in current flow between the first and second electrode arrangements. This in turn leads to a large measured coefficient of variation in the properties of the particles.

It is an aim of the present invention to obviate or reduce the above mentioned problem.

Accordingly, the present invention provides apparatus for electrically measuring individual particles flowing in a liquid, which apparatus comprises:
(i) a fluidic channel for receiving a liquid having the individual particles in suspension in the liquid;
(ii) a first electrode arrangement having at least one measurement electrode and at least one signal electrode;
(iii) at least one other electrode arrangement having at least one measurement electrode and at least one signal electrode;
(iv) at least one signal conditioning electrode which is positioned between the measurement electrode of the first electrode arrangement and the measurement electrode of the other electrode arrangement; and
(v) an electronic circuit for measuring signal changes;
and the apparatus being such that
(vi) the first and the other electrode arrangements are connected to the electronic circuit whereby individual particles passing between the first and other electrode arrangements cause a change in electrical signal which is measured; and
(vii) the electrical potential of the signal conditioning electrode is controlled to substantially prevent current flow between the first electrode arrangement and the other electrode arrangement.

The apparatus of the present invention is such that the first and other electrode arrangements enable a differential mode of operation which reduces noise and artefacts. The signal conditioning electrode which is held at the same voltage as the measurement electrodes prevents current flow between the first electrode arrangement and the other electrode arrangement and thereby helps to prevent errors in the impedance signal when individual particles flow off-centre through the fluidic channel, whereby the measured impedance signal of the individual particles is of an improved accuracy as compared with the measured impedance signal that would be obtained without the signal conditioning electrode held at the same voltage as the measurement electrode. The apparatus of the present invention is advantageously able to provide high accuracy measurements without unnecessary complications to the construction of the apparatus.

The apparatus of the present invention may operate such that the first and other electrode arrangements act as sensor electrodes, with the signal conditioning electrode held at the same voltage as the measurement electrodes preventing the current flowing between first and other electrode arrangements from interfering with the measured current due to the passage of the individual particles through the channel.

US 2010/006441 discloses apparatus for electrically measuring individual particles flowing in a liquid, with the apparatus comprising of a fluidic channel for receiving the liquid having the individual particles in suspension in the liquid, first and second electrode arrangements, and supplementary electrodes which are used in a guard configuration to restrict the measurement volume. These supplementary electrodes do not act as signal conditioning electrodes for reducing particle positional dependence as in the present invention. Guard electrodes provide a uniform field within a channel. The electric field in the present invention is non-uniform. In the present invention it is the change in electric field as a particle passes through the apparatus that is of importance. The apparatus of the present invention operates to increase measurement accuracy for individual particles which are not flowing through the centre of the apparatus, and the signal conditioning electrode of the present invention is not employed to restrict measurement volume. When the apparatus of the present invention includes one or more signal conditioning electrodes held at the same voltage as the measurement electrode, then it is believed to be highly unexpected and very counter-intuitive to realise that it is beneficial to hold all the signal conditioning electrodes at the same voltage as one another. With guard electrodes, the field lines would be nicely parallel, whereas with signal conditioning electrodes, the field lines diverge from the signal electrodes, which would be expected to give very poor results. The present invention is based on an understanding that the benefits of the signal conditioning electrodes are due to restriction of the cross-path of electrical current that flows between the two arrangements of electrodes when a particle moves in the fluidic channel.

The apparatus of the present invention may be one which includes a signal processing algorithm that matches measured impedance signals against a template in order to obtain an estimate of the position of each particle as the particle passes through the fluidic channel, and in which the apparatus comprises a compensation algorithm for using the estimate to compensate obtained electrical signals for off-centre individual particles and thereby further increase achieved measurement accuracy of the individual particles. The template may provide fluctuations obtained using simulations. The template may provide other information and/or use another basis for the information provided.

The apparatus may be one in which the signal conditioning electrode is positioned between the measurement electrode of the first electrode arrangement and the measurement electrode of the other electrode arrangement.

The apparatus may be one in which there are three of the signal conditioning electrodes, with one of the signal conditioning electrodes being positioned on each side of the measurement electrode of the first electrode arrangement and the measurement electrode of the other electrode arrangement. If desired, the two outer ones of these three signal conditioning electrodes may be omitted.

The apparatus of the present invention may be one in which there is one of the signal conditioning electrodes positioned between the signal electrode of the first electrode arrangement and the signal electrode of the other electrode arrangement. In this case, there may be three of the signal conditioning electrodes for the signal electrodes, with one of the three signal conditioning electrodes being positioned on each side of the signal electrode of the first electrode arrangement and the signal electrode of the other electrode arrangement. If desired, the outer two of these three signal conditioning electrodes for the signal electrodes may be omitted.

In variations of the apparatus of the present invention as described above, all of the electrode configurations may be doubled up, so that each stated signal conditioning electrode is replaced by two signal conditioning electrodes. In this case, each two signal conditioning electrodes may form a set, and the voltage for each set may be the same as or different from the voltage in another set or sets.

Preferably, the apparatus is one in which the signal electrodes of the first and other electrode arrangements are driven by a voltage source, whereby the measured signal is based on a current. The voltage source may be of variable frequency. If desired, the apparatus may be one in which the signal electrodes of the first and other electrode arrangements are driven by a current source, whereby the measured current is based on a voltage.

Preferably, the apparatus is one in which the first and other electrode arrangements are metal electrode arrangements. The metal electrodes of each of the first and other metal electrode arrangements may be positioned in the fluidic channel. The metal electrodes of each of the first and other metal electrode arrangements may be positioned in the fluidic channel and opposite each other. Other locations for the metal electrodes of each of the first and other metal electrode arrangements may be employed.

The metal electrodes of each of the metal electrode arrangements may be similar in size to the particles to be measured, for example 1-100 μm wide, for example for biological cells. Other measurements for the metal electrodes of each of the metal electrode arrangements may be employed.

Alternatively, the apparatus may be one in which the first and other electrode arrangements are liquid electrode arrangements. The liquid electrode arrangements may be provided in an electrode channel which is additional to the fluidic channel. Other configurations for the liquid electrode arrangements may be employed.

Alternatively, the first and other electrode arrangements may be gel electrode arrangements.

Preferably, the apparatus is one in which the fluidic channel is rectilinear in cross section. The fluidic channel may be square in cross section. The fluidic channel may alternatively be substantially rectangular in cross section.

The apparatus may be one in which the electrodes each span a wall, and each electrode arrangement spans two opposing walls, and the signal conditioning electrode helps to reduce errors in the signal for particles flowing non-equidistant between the electrodes of the electrode arrangements. The first electrode arrangement and the other electrode arrangement may be arranged on the same walls as one another.

The fluidic channel may be 1-100 μm by 1-100 μm in cross section. Other cross sectional shapes for the fluidic channel may be employed.

The signal conditioning electrode may provide an earth voltage. Alternatively, the signal conditioning electrode may provide a voltage which is that of either of the measurement electrodes of the first and other electrode arrangements. Thus the voltage of the signal conditioning electrode does not have to be through earth.

The apparatus of the present invention may include a conducting gel wall.

The apparatus of the present invention may include the liquid. The liquid may be an electrolyte and/or an oil. Other types of liquid able to suspend the particles may be employed.

The apparatus of the present invention may be used in a wide variety of technical areas where there is a requirement for high accuracy dielectric measurements of any small particles. Thus, for example, the apparatus of the present invention may be used to measure individual particles in the form of cells, bacteria, phytoplankton, trypanosomes, dust particles, or other appropriate objects. By way of example, it is mentioned that the apparatus of the present invention may be used for a point-of-care full blood count. The counting and discrimination of different cell types is often diagnostically important. Also important is the measuring of the distribution width of populations of cells, which requires a high accuracy measurement. Other examples of uses of the present invention are for platelet measurements, which may be required as part of a point-of-care test for liver fibrosis for patients with liver fibrosis. Still further, the apparatus of the present invention may be used to provide high accuracy measurements of pollen and dust in ice cores, which are needed to date and analyse samples for environmental analysis. Hitherto, only discrete measurements could be formed on a Coulter counter, but continuous flow measurements are required. Still further, the present invention is easy to integrate with many other existing types of apparatus such for example as on-the-fly sample pre-processing (including cell labelling or pre-enrichment) for a wide variety of applications.

Embodiments of the invention will now be described solely by way of example and with reference to the accompanying drawings in which:

FIG. 1 is a circuit diagram of known apparatus for electrically measuring individual particles flowing in a liquid;

FIG. 2 is a view like FIG. 1 but shows the apparatus of FIG. 1 in more detail;

FIG. 3 is a circuit diagram of known apparatus for electrically measuring individual particles flowing in a liquid in a guard electrode configuration;

FIG. 4 is a view like FIG. 3 but shows the apparatus of FIG. 3 in more detail;

FIG. 5 shows apparatus of the present invention for electrically measuring individual particles flowing in a liquid;

FIG. 6 is a view like FIG. 5 but shows the apparatus of FIG. 5 in more detail;

FIG. 7 is a simulated variation in particle impedance with position, and shows the variation for the known standard electrode design shown in FIG. 1 and FIG. 2, for the known guard electrode configuration shown in FIG. 3 and FIG. 4, and for the new electrode design shown in FIG. 5 and FIG. 6;

FIG. 8 shows a side view of the apparatus in FIGS. 1 and 2 in more detail;

FIG. 9 illustrates individual particles passing through part of the apparatus shown in FIG. 8, and also shows an example signal for the particle positions shown in FIG. 9;

FIG. 10 is like FIG. 8 but shows a side view of the apparatus in FIGS. 5 and 6 in more detail;

FIG. 11 illustrates individual particles passing through part of the apparatus shown in FIG. 10, and also shows an example signal for the particle positions shown in FIG. 11;

FIG. 12 shows simulated differential current for individual particles of different sizes and obtained in the standard 4 electrode geometry;

FIG. 13 shows simulated differential current for individual particles of different sizes and obtained in the guard electrode configuration;

FIG. 14 shows simulated differential current for individual particles of different sizes and obtained with the use the new signal conditioning electrodes shown in FIGS. 5 and 6;

FIG. 15 is a histogram of the experimentally measured impedance for a sample containing different sizes of individual particles and in a standard 4 electrode configuration shown in FIGS. 1 and 2;

FIG. 16 is a histogram like that shown in FIG. 13 but obtained with the use of the signal conditioning electrodes;

FIG. 17 is a density plot of measured impedance of a sample containing individual particles of different sizes, and shows the estimated bead height in the channel as found by fitting each experimental peak with simulated peak spectra;

FIG. 18 is a histogram of the impedance of individual particles of different sizes after correction for positional dependence;

FIG. 19a-19c show different positions for signal electrodes, measurement electrodes and signal conditioning electrodes in apparatus of the present invention;

FIG. 20 illustrates a first method of operation with the apparatus of the present invention; and FIG. 21 illustrates a second method of operation with the apparatus of the present invention.

Referring to FIGS. 1 and 2, there is shown known apparatus 1 for electrically measuring individual particles 4 flowing in a liquid 6. The apparatus 1 comprises a fluidic channel 5 for receiving a liquid 6 having the individual particles in suspension in the liquid 6. The apparatus 1 also comprises a first electrode arrangement 8 having a measurement electrode 16 and a signal electrode 11. The apparatus 1 further comprises another electrode arrangement in the form of a second electrode arrangement 9 having a measurement electrode 18 and a signal electrode 13.

The apparatus 1 is such that the measurement electrodes 16, 18 are connected to an amplifier, whereby individual particles passing between the first and second electrode arrangements 8, 9 cause a change in electrical current which is measured and recorded as an impedance signal. This measurement is effected using current to voltage means 20 connected to the measurement electrode 16 of the first electrode arrangement 8, and current to voltage means 21 connected to the measurement electrode 18 of the second electrode arrangement 9. The two current to voltage means 20, 21 connect to a differential amplifier 22 which provides an output voltage 23. FIG. 1 shows the two current to voltage means 20, 21 and the differential amplifier 22 in block diagram form. FIG. 2 shows in more detail the two current to voltage means 20, 21 and the differential amplifier 22. More specifically, as can be seen in FIG. 2, each current to voltage means 20, 21 comprises a resistor 24 and an operational amplifier 25. The differential amplifier 22 comprises four resistors 26 connected as shown to an operational amplifier 27.

As can be seen from both FIGS. 1 and 2, the signal electrodes 11, 13 of the first and second electrode arrangements 8, 9 are fed with an alternating current voltage source 7.

The apparatus 1 operates such that the signal electrodes 11, 13 are driven from the alternating current voltage source 7 which may be of variable frequency. The particles 4 pass in a gap 28 between the first and second electrode arrangements 8, 9. The change in electrical current is measured and recorded as an impedance signal. Two electrode arrangements 8, 9 are employed as opposed to just one electrode arrangement to enable a differential mode of operation, which reduces noises and artefacts. However, there are still limitations as to the quality of data provided by the apparatus 1. In particular, this has to do with the fact that the impedance signal depends on the absolute position of the measured individual particle 4 within the detection volume. A particle 4 travelling close to the electrodes of the first and second electrode arrangements 8, 9 has a higher measured impedance compared to the same sized particle 4 travelling through the centre of the fluidic channel 5. This is because the particle 4 distorts the electrical field between the measurement electrode arrangements 8, 9. This particle positional dependence leads to a very large measured coefficient of variation in particle properties, with this very large measured coefficient of variation being much larger than in reality.

The above mentioned problem with the known apparatus 1 is overcome by the apparatus 3 which is of the present invention and which is shown in FIGS. 5 and 6. FIGS. 5 and 6 are similar to FIGS. 1 and 2 and similar parts have been given the same reference numerals for ease of comparison and understanding.

The apparatus 3 is such that it includes signal conditioning electrodes. More specifically, there is a signal conditioning electrode 17 provided between the measurement electrode 16 of the first electrode arrangement 8, and the measurement electrode 18 of the second electrode arrangement 9. As can be seen from FIGS. 5 and 6, the signal conditioning electrode 17 is one of three signal conditioning electrodes 15, 17, 19 employed for the measurement electrodes 16, 18. The position of the signal conditioning electrodes 15, 17, 19 is such that there is one of the signal conditioning electrodes 15, 17, 19 positioned on each side of the measurement electrode 16 of the first electrode arrangement 8 and the measurement electrode 18 of the second electrode arrangement 9.

The apparatus 3 is such that there is a signal conditioning electrode 12 positioned between the signal electrode 11 of the first electrode arrangement 8 and the signal electrode 13 of the second electrode arrangement 9. As can be seen from FIGS. 5 and 6, the signal conditioning electrode 12 is one of three signal conditioning electrodes 10, 12, 14 employed for the signal electrodes 11, 13. The arrangement of the signal conditioning electrodes 10, 12, 14 is such that there is one of the three signal conditioning electrodes 10, 12, 14 positioned on either side of the signal electrode 11 of the first electrode arrangement 8, and the signal electrode 13 of the second electrode arrangement 9.

The first and second electrode arrangements 8, 9 are metal electrode arrangements. As can be seen from FIGS. 5 and 6, the first and second metal electrode arrangements 8, 9 are positioned in the fluidic channel 5 and such that the metal electrodes of each of the first and second metal electrode arrangements 8, 9 are positioned in the fluidic channel 5 and opposite each other. By way of example only, it is mentioned that the metal electrodes of each of the first and second electrode arrangements 8, 9 may be 20-40 µm wide.

The fluidic channel 5 is rectilinear in cross section. More specifically, the fluidic channel 5 is square in cross section. By way of example only, it is mentioned that the fluidic channel 5 may typically be 40 µm by 40 µm.

The signal conditioning electrodes 10, 12, 14, 15, 17 and 19 provide an earth voltage. In an alternative embodiment of the invention, the signal conditioning electrodes 10, 12, 14, 15, 17 and 19 may provide a voltage which is that of either of the measurement electrodes 16, 18 of the first and second electrode arrangements 8, 9.

FIG. 3 and FIG. 4 show how the fluidic channel 5 would look using known guard electrodes instead of the signal conditioning electrodes. The known guard electrodes are identified by the same numbers as the signal conditioning electrodes but with the addition of the letter "a".

Use of the signal conditioning electrodes 10, 12, 14, 15, 17 and 19 is different from the use of the guard electrodes 10a, 12a, 14a, 15a, 17a and 19a. The signal conditioning electrodes 10, 12, 14, 15, 17 and 19 are held at the same voltage as the measurement electrodes 16, 18. In contrast, at least some of the guard electrodes 10a, 12a, 14a, 15a, 17a and 19a will not be at the same voltage as their closest measurement electrode 16, 18. It is believed to be highly unexpected and very counter-intuitive to realise that it is beneficial to hold all the signal conditioning electrodes 10, 12, 14, 15, 17 and 19 at the same voltage as one another and the same as the measurement electrodes. With the guard electrodes 10a, 12a, 14a, 15a, 17a and 19a, the field lines are nicely parallel. However, with the signal conditioning electrodes 10, 12, 14, 15, 17 and 19, the field lines diverge from each of the signal electrodes 11, 13, which would be expected to give very poor results. From a consideration of the cross-path electrical flows possible due to blockage by an individual particle 4, it has been appreciated that this is not the case. The signal conditioning electrodes 10, 12, 14, 15, 17 and 19 advantageously prevent the first and second electrode arrangements 8, 9 interfering during the passage of an individual particle 4 through the gap 28 in the fluidic channel 5.

FIG. 7 shows the simulated variation in impedance of individual particles 4 with position in the fluidic channel 5 for the known apparatus 1 shown in FIGS. 1 and 2, the known apparatus 2 shown in FIGS. 3 and 4, and the apparatus 3 of the present invention shown in FIGS. 5 and 6. It will be seen from FIG. 7 that the apparatus 3 of the present invention is considerably superior in operation in that there is a much reduced variation in particle impedance with the position of the individual particles 4 in the fluidic channel 5.

FIG. 8 shows an overview of operation of apparatus 30 of the present invention. The apparatus 30 is such that it has a fluidic channel 31 formed between two layers of glass 32, 34. The two layers of glass 32, 34 are separated by an epoxy-based negative photoresist known as SU-8. The SU-8 layer 33 defines the height of the fluidic channel 31. By way of non-limiting example it is mentioned that the glass layers 32, 34 may be 0.7 mm thick, and the layer 33 may be 40 µm thick. Also by way of non-limiting example, it is mentioned that the fluidic channel 31 may be such that it is 40 µm wide, and may have electrodes 10-19, which are 30 µm wide and separated by a gap which is 10 µm wide.

As shown in FIG. 8, the individual particles 4 are in a liquid 6 in a sample container 35. The sample container 35 comprises a piston 36 for forcing the liquid 6 through an outlet 37 in the sample container 35. The electrodes 16, 18 are measurement electrodes which are each connected to a current to voltage amplifier 20 and 21, which in turn is connected to a differential amplifier 22. When the liquid 6 with the individual particles 4 has passed through the fluidic channel 31, the liquid 6 is passed as waste to a waste outlet 38.

In operation of the apparatus 30, the solution of particles 4 to be measured is driven through the apparatus 30. The liquid 6 is diluted such that only one particle 4 is between the electrodes 10-19 at any time. An AC voltage 7 is applied to the top two signal electrodes 11, 13. The difference in current passing through the bottom two measurement electrodes 16, 18 is measured as impedance.

FIG. 9 shows that as a particle 4 passes between the electrodes 10-19, from t=t0 to t4, the impedance signal goes from positive and then negative. The maximum peak of the signal is shown as a, and this maximum peak is equal to the minimum of the trough, also shown as a. The maximum of the signal a is recorded, and is proportioned to the volume (size) of the particle 4.

FIGS. 10 and 11 are like FIGS. 8 and 9, but show the standard electrode geometry design.

FIG. 12 shows simulated differential current for a 10 µm diameter individual particle 4 passing through the apparatus 1 shown in FIGS. 1 and 2. It will be seen that there are considerable variations in measurements.

FIG. 13 is like FIG. 12 but shows a simulated differential current for a 10 µm diameter individual particle 4 when measured using the apparatus 2 shown in FIGS. 3 and 4. It will be seen that there are considerable variations in measurements.

FIG. 14 is like FIG. 12 but shows a simulated differential current for a 10 µm diameter individual particle 4 when measured using the apparatus 3 shown in FIGS. 5 and 6. It will be seen that the variations in height of the individual particle 4 are much reduced.

FIG. 15 is a histogram of experimentally measured impedance of a sample containing 3, 4.5, 6 and 10 µm diameter polystyrene beads measured using known apparatus 1 of the type shown in FIGS. 1 and 2.

FIG. 16 is a similar histogram to that shown in FIG. 15 but FIG. 16 shows the histogram obtained using apparatus similar to the apparatus 3 of the present invention and as shown in FIGS. 5 and 6.

FIG. 17 is a density plot of the measured impedance of a sample containing 3, 4.5, 6 and 10 µm beads. The bead height within the fluidic channel 5 is determined by fitting simulations to each event spectra.

In another embodiment of the present invention, the apparatus of the present invention is provided with a signal processing algorithm that matches measured impedance signals against a template in order to obtain an estimate of the position of each individual particle 4 as the individual particle 4 passes through the fluidic channel 5. In this case, the apparatus of the present invention may comprise compensation means for using the estimate to compensate obtained electrical signals for the off-centre individual particles and thereby further to increase achieved measurement accuracy of the individual particles. The template used may be one that provides fluctuations obtained using simulation.

The use of a signal processing algorithm thus enables a further improvement in measurements. This is done by matching the measured impedance signals against the template functions obtained using the simulations. This provides an estimate of the position of each individual particle 4 as it passes through the fluidic channel 5. This information is then used to further reduce particle positional dependence and to increase the measurement accuracy.

By way of example, each individual event spectra in the data set of FIG. 16 was compared with a set of templates obtained using simulations. This provided an estimate of height for each individual particle 4 as the individual particle 4 passed through the fluidic channel 5. The measured impedance was plotted against the estimated bead height shown in FIG. 17, and shows that individual particles 4 travelling close to the electrodes have a slightly higher impedance signal compared to those travelling through the centre of the fluidic channel 5 (bead height=15µ). This function can be approximated using a polynomial, which is then used to correct for the positional dependence. The correction factor is based on the estimated bead height within the channel and corrects for particle positional dependence.

FIG. 18 shows the data presented in FIG. 16 but after correction for position using the signal processing algorithm. The mean and standard deviation, as calculated from a best-fit Gaussian, is compared to the manufacturer's data in the following table.

| Nominal Diameter (µm) | Manufacturer's data | | | Experimental data | | |
| --- | --- | --- | --- | --- | --- | --- |
| | Diameter (µm) | S. dev. | C.V. | Diameter (µm) | S. dev. | C.V. |
| 3 | 3.11 | 0.088 | 2.83 | 3.15 | 0.049 | 1.53 |
| 4.5 | 4.42 | 0.172 | 3.89 | 4.29 | 0.050 | 1.16 |
| 6 | 6.07 | 0.193 | 3.18 | 5.80 | 0.077 | 1.33 |
| 10 | 10.17 | 0.304 | 2.99 | 10.16 | 0.100 | 0.98 |

FIGS. 19a, 19b and 19c show different relative positions for signal electrodes, measurement electrodes and signal conditioning electrodes in apparatus of the present invention.

FIG. 20 shows the following three steps for measuring electrical signals and generating a comparison signal.

Step 1: Measure the electrical signals flowing into M1 and M2 and generate a comparison signal (a). This is a first order assessment of the electrical properties of the particle.

Step 2: Measure the signals flowing into M2 and M3 and generate a comparison signal (b).

Step 3: Apply a second order assessment/correction to the comparison signal in step 1 based on the time between peak and trough in step 1 (time t2–time t1), compared to the time between peak and trough in step 2 (t3–t2).

FIG. 21 shows the following three steps for measuring electrical signals and generating a comparison signal.

Step 1: Measure the electrical signals flowing into M1 and M2 and generate a comparison signal (a). This is a first order assessment of the electrical properties of the particle.

Step 2: Measure the electrical signal M3.

Step 3: Apply a second order assessment/correction to the comparison signal in step 1 based on a height-related feature (for example the height h of the trough at t3) from step 2.

The apparatus of the present invention is able to be manufactured in a relatively simple manner. It enables simple microfluidic impedance analysis to operate without sheath flow particle positioning. The apparatus of the present invention is able to provide multi-frequency analysis, it can process small volumes, and it can operate continuously, integrated with microfluidic continuous sample pre-processing if needed. Hitherto, the commercial solution to electrical measurements of single particles was a Coulter counter, where particle volume is determined from the change in electrical current as a particle travels through an orifice. In this case, the electrodes are large and are far away from the orifice, and the Coulter counter has a limited frequency range due to parasitic capacitances. The present invention provides a good commercial alternative to the Coulter counter. In particular, with the use of its miniature electrodes in its microfluidic channel, the apparatus of the present invention can be used at much higher frequencies, which enable the measurement of cell membranes and cytoplasm conductivity. The apparatus of the present invention is also easier to integrate with any other systems than a Coulter counter.

It is to be appreciated that the embodiments of the invention described above with reference to the accompanying drawings have been given by way of example only and that modifications may be effected. Thus, for example, instead of using metal electrodes in the first and second electrode arrangements, the apparatus of the present invention may use liquid electrodes or gel electrodes. The signal electrodes 11, 13 in the first and second electrode arrangements 8, 9 may be driven by a current source, with the measured signal being based on a voltage measurement. If the spacing between the measurement electrodes on the one hand and the signal electrode on the other hand is increased sufficiently, then, for example, twice the amount of signal conditioning electrodes may be employed between the measurement electrodes and/or the signal electrodes. The end signal conditioning electrodes 10, 14, 15, 19 may be omitted. Also, the electrodes need not be on the same wall as shown and one arrangement of electrodes could be polarity reversed, this being because the arrangements are electrically independent due to the use of the central signal conditioning electrodes 12, 17. Individual components shown in the drawings are not limited to use in their drawings and they may be used in other drawings and in all aspects of the invention.

The invention claimed is:

1. Apparatus for electrically measuring individual particles flowing in a liquid, which apparatus comprises:
   (i) a fluidic channel for receiving a liquid having the individual particles in suspension in the liquid;
   (ii) a first electrode arrangement having at least one measurement electrode and at least one signal electrode;
   (iii) at least one other electrode arrangement having at least one measurement electrode and at least one signal electrode;
   (iv) at least one signal conditioning electrode which is positioned between the measurement electrode of the first electrode arrangement and the measurement electrode of the other electrode arrangement; and
   (v) an electronic circuit for measuring signal changes;
and the apparatus being such that:
   (vi) the first and the other electrode arrangements are connected to the electronic circuit whereby individual particles passing between the first and other electrode arrangements cause a change in electrical signal which is measured; and (vii) the electrical potential of the signal conditioning electrode is controlled to substantially prevent current flow between the first electrode arrangement and the other electrode arrangement.

2. Apparatus according to claim 1 and including a signal processing algorithm that matches measured impedance signals against a template in order to obtain an estimate of the position of each particle as the particle passes through the fluidic channel, and in which the apparatus comprises a compensation algorithm for using the estimate to compensate obtained electrical signals for off-centre individual particles and thereby further to increase achieved measurement accuracy of the individual particles.

3. Apparatus according to claim 2 in which the template provides fluctuations obtained using simulations.

4. Apparatus according to claim 1 in which the signal electrodes of the first and other electrode arrangements are driven by a voltage source, whereby the measured signal is based on a current.

5. Apparatus according to claim 1 in which the signal electrodes of the first and other electrode arrangements are driven by a current source, whereby the measured signal is based on a voltage.

6. Apparatus according to claim 1 in which the first and other electrode arrangements are metal electrode arrangements.

7. Apparatus according to claim 6 in which the metal electrodes of each of the first and other metal electrode arrangements are positioned in the fluidic channel.

8. Apparatus according to claim 7 in which the metal electrodes of each of the first and other metal electrode arrangements are positioned in the fluidic channel and opposite each other.

9. Apparatus according to claim 8 in which the metal electrodes of each of the metal electrode arrangements are 1-100 μm wide.

10. Apparatus according to claim 1 in which the first and other electrode arrangements are liquid electrode arrangements.

11. Apparatus according to claim 10 in which the liquid electrode arrangements are provided in an electrode channel which is additional to the fluidic channel.

12. Apparatus according to claim 1 in which the first and other electrode arrangements are gel electrode arrangements.

13. Apparatus according to claim 1 in which the fluidic channel is substantially rectilinear in cross section.

14. Apparatus according to claim 1 in which the electrodes each span a wall, and each electrode arrangement spans two opposing walls, and the signal conditioning electrode helps to reduce errors in the signal for particles flowing non-equidistant between the electrodes of the electrode arrangements.

15. Apparatus according to claim 14 in which the first electrode arrangement spans the same two opposing walls as the other electrode arrangement.

16. Apparatus according to claim 1 in which the fluidic channel is 1-100 μm by 1-100 μm in cross section.

17. Apparatus according to claim 1 in which the signal conditioning electrode provides an earth voltage.

18. Apparatus according to claim 1 in which the signal conditioning electrode provides a voltage which is that of either of the measurement electrodes of the first and other electrode arrangements.

19. Apparatus according to claim 1 and including a conducting gel wall.

* * * * *